United States Patent
Faris et al.

(10) Patent No.: US 6,544,742 B1
(45) Date of Patent: Apr. 8, 2003

(54) DETECTION OF GENES REGULATED BY EGF IN BREAST CANCER

(75) Inventors: Mary Faris, Los Angeles, CA (US); David G. Streeter, Boulder Creek, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 88 days.

(21) Appl. No.: 09/653,119

(22) Filed: Aug. 31, 2000

Related U.S. Application Data

(60) Provisional application No. 60/152,548, filed on Sep. 3, 1999.

(51) Int. Cl.$^7$ .............................. C12Q 1/68; C12P 19/34; C07H 21/04
(52) U.S. Cl. ..................... 435/6; 435/91.1; 435/91.2; 536/23.1; 536/24.3
(58) Field of Search ....................... 435/6, 91.1, 287.2, 435/91.2; 536/23.1, 24.3

(56) References Cited

PUBLICATIONS

Khazaie, K., et al. "EGF receptor in neoplasia and metastasis", Cancer Metastasis Rev, 12(3–4):255–74 (1993).

Nicolson, Garth L., "Cell surface molecules and tumor metastasis, Regulation of metastatic phenotypic diversity", Exp Cell Res 150(1):3–22 (1984).

Schirrmacher, Volker, "Cancer metastasis: experimental approaches, theoretical concepts, and impacts for treatment strategies", Adv Cancer Res, 43:1–73 (1985).

Gish, Kurt, "Breast Cancer Surveying half the human genome with transcription profiling for better diagnosis, prognosis, and therapy", Awis Magazine, 28(3): 7–10 (1999).

Genbank accession No. 4500003, Feb. 18, 2000.*

Genbank accession No. 180947, Jan. 21, 1994.*

Genbank Accession No. 531159, Aug. 20, 1994.*

\* cited by examiner

Primary Examiner—W. Gary Jones
Assistant Examiner—Jehanne Souaya
(74) Attorney, Agent, or Firm—Incyte Genomics, Inc.

(57) ABSTRACT

The present invention relates to a combination comprising a plurality of polynucleotide probes that are modulated in response to EGF and which are associated with breast cancer, and which may be used in their entirety or in part as to diagnose, to stage, to treat, or to monitor the treatment of a subject with a breast cancer.

6 Claims, No Drawings

SEQUENCE LISTING

<160> NUMBER OF SEQ ID NOS: 16

<210> SEQ ID NO 1
<211> LENGTH: 260
<212> TYPE: DNA
<213> ORGANISM: Homo sapiens
<220> FEATURE:
<221> NAME/KEY: misc_feature
<223> OTHER INFORMATION: Incyte ID No: 2027812H1
<221> NAME/KEY: unsure
<222> LOCATION: 78, 192
<223> OTHER INFORMATION: a, t, c, g, or other

<400> SEQUENCE: 1
cagaattctg ctgtttctag atccaaactt ttcccatccc agcatatggt tatttataat     60
aatacactta gtaagttngt gggtggtgga ggggaaggac agattgggac aggaagcaat    120
gtggcttatg tctcatctct taaagggtaa gccatgcatc ctatgcttct tggaccctgt    180
cccctgcctt gncccctagta cctagctccc cccagtacct agctcctccc ctcagtaagg    240
agctcccctc agtacctagc                                                 260

<210> SEQ ID NO 2
<211> LENGTH: 267
<212> TYPE: DNA
<213> ORGANISM: Homo sapiens
<220> FEATURE:
<221> NAME/KEY: misc_feature
<223> OTHER INFORMATION: Incyte ID No: 2070554H1

<400> SEQUENCE: 2
cagaaatgga ttcgaaatat cagtgtgtga agctgaatga tggtcacttc atgcctgtcc     60
tgggatttgg cacctatgcg cctgcagagg ttcctaaaag taaagcttta gaggccacca    120
aattggcaat tgaagctggc ttccgccata ttgattctgc tcatttatac aataatgagg    180
agcaggttgg actggccatc cgaagcaaga ttgcagatgg cagtgtgaag agagaagaca    240
tattctacac ttcaaagctt tggtgca                                         267

<210> SEQ ID NO 3
<211> LENGTH: 466
<212> TYPE: DNA
<213> ORGANISM: Homo sapiens
<220> FEATURE:
<221> NAME/KEY: misc_feature
<223> OTHER INFORMATION: Incyte ID No: 1645856F6
<221> NAME/KEY: unsure
<222> LOCATION: 196
<223> OTHER INFORMATION: a, t, c, g, or other

<400> SEQUENCE: 3
tgcagagctt gtggaggcca tggggcgcgt cgtcgcggac tcgtctcctc gctgctgggg     60
ttgtggctgt tgctgtgcag ctgcggatgc cccgagggcg ccgagctgcg tgctccgcca    120
gataaaatcg cgattattgg agccggaatt ggtggcactt cagcagccta ttacctgcgg    180
cagaaatttg gaaanatgt gaagatagac ctgtttgaaa gagaagaggt cggggggccgc    240 ctggctacca tgatggtgca ggggcaagaa tacgaggcag gaggttctgt catccatcct    300
ttaaatctgc acatgaaacg ttttgtcaaa gacctgggtc tctctgctgt tcaggcctct    360
ggtggcctac tggggatata taatgagag actctgtat tgaggagag caactggttc    420 ataattaacg tgattaaatt agtttggcgc tatgggattc aatccc                    466

<210> SEQ ID NO 4
<211> LENGTH: 454
<212> TYPE: DNA
<213> ORGANISM: Homo sapiens
<220> FEATURE:
<221> NAME/KEY: misc_feature
<223> OTHER INFORMATION: Incyte ID No: 1297817F6
<221> NAME/KEY: unsure
<222> LOCATION: 148-149, 153, 436
<223> OTHER INFORMATION: a, t, c, g, or other

<400> SEQUENCE: 4

| | | | | | | |
|---|---|---|---|---|---|---|
| cgcaggcccc | gagaactgtc | gcccttccac | gatgtggctc | cgtgccttta | tcctggccac | 60 |
| tctctctgct | tccgcggctt | gggcagggca | tccgtcctcg | ccacctgtgg | tggacaccgt | 120 |
| gcatggcaaa | gtgctgggga | agttcgtnnc | ccnaagctta | gaaggatttg | cacagcctgt | 180 |
| ggccattttc | ctgggaatcc | cttttgccaa | gccgcctctt | ggaccnctga | ggtttactcc | 240 |
| accgcagcct | gcagaaccat | ggagctttgt | gaagaatgcc | acctcgtacc | ctcctatgtg | 300 |
| cacccaagat | cccaaggcgg | ggcagttact | ctcagagcta | tttacaaacc | gaaggagaa | 360 |
| cattcctctc | aagtttctga | agactgtctt | tactcaatat | ttacatcctg | ctgacttgac | 420 |
| caaggaaaaa | caggtngccg | gtgatggtgt | ggat | | | 454 |

<210> SEQ ID NO 5
<211> LENGTH: 236
<212> TYPE: DNA
<213> ORGANISM: Homo sapiens
<220> FEATURE:
<221> NAME/KEY: misc_feature
<223> OTHER INFORMATION: Incyte ID No: 086625H1
<221> NAME/KEY: unsure
<222> LOCATION: 119, 156
<223> OTHER INFORMATION: a, t, c, g, or other

<400> SEQUENCE: 5

| | | | | | | |
|---|---|---|---|---|---|---|
| cggacagaca | gagtgcactg | ccgggtgctg | cctaaccatg | cctggagact | ggaccgcagc | 60 |
| catgttgggg | ccccgatgcc | gtgcaattta | ataaaacttg | ttgatgtgga | agaaatgant | 120 |
| tacatggctg | ccgagggcga | gggcgaggtg | tgtgtnaaag | ggccaaatgt | atttaagggc | 180 |
| tacttgaagg | acccagcgaa | aacagcagaa | gctttggaca | agacggctg | gttaca | 236 |

<210> SEQ ID NO 6
<211> LENGTH: 511
<212> TYPE: DNA
<213> ORGANISM: Homo sapiens
<220> FEATURE:
<221> NAME/KEY: misc_feature
<223> OTHER INFORMATION: Incyte ID No: 2888464F6
<221> NAME/KEY: unsure
<222> LOCATION: 471
<223> OTHER INFORMATION: a, t, c, g, or other

<400> SEQUENCE: 6

| | | | | | | |
|---|---|---|---|---|---|---|
| cttattttat | ttttaagctc | aaactgctta | agaatacctt | aattccttaa | agtgaaataa | 60 |
| ttttttgcaa | aggggtttcc | tcgatttgga | gctttttttt | tcttccaccg | tcatttctaa | 120 |
| ctcttaaaac | caactcagtt | ccatcatggt | gatgttcaag | aagatcaagt | cttttgaggt | 180 |
| ggtctttaac | gaccctgaaa | aggtgtacgg | cagtggcgag | aaggtggctg | gccgggtgat | 240 |
| agtggaggtg | tgtgaagtta | ctcgtgtcaa | agccgttagg | atcctggctt | gcggagtggc | 300 |
| taaagtgctt | tggatgcagg | gatcccagca | gtgcaaacag | acttcggagt | acctgcgcta | 360 |
| tgaagacacg | cttcttctgg | aagaccagcc | aacaggtgag | aatgagatgg | tgatcatgag | 420 |

```
acctggaaac aaatatgagt acaagttcgg ctttgagctt cctcagggc ntctgggaac    480 atccttcaaa ggaaaatatg ggtgtgtaga c                                  511
```

<210> SEQ ID NO 7
<211> LENGTH: 410
<212> TYPE: DNA
<213> ORGANISM: Homo sapiens
<220> FEATURE:
<221> NAME/KEY: misc_feature
<223> OTHER INFORMATION: Incyte ID No: 2125344F6

<400> SEQUENCE: 7

```
gcggccgcgg cggcagcaga ccccagagtc agaaggagtg agaaccctga cccctaatcc    60
cactgcatcc agccaatagg agcccagcca ccatggcgga gtgcaggagg tgcagatcac   120
agaggagaag ccactgttgc caggacagac gcctgaggcg gccaagactc actctgtgga   180
gacaccatac ggctctgtca ctttcactgt ctatggcacc cccaaaccca acgcccagc    240 gatccttacc taccacgatg tgggactcaa ctataaatct tgcttccagc cactgtttca   300
gttcgaggac atgcaggaaa tcattcagaa ctttgtgcgg gttcatgtgg atgccctgga   360
atggaagagg gagccctgtg ttcccttttgg gatatcagta acccatctct             410
```

<210> SEQ ID NO 8
<211> LENGTH: 386
<212> TYPE: DNA
<213> ORGANISM: Homo sapiens
<220> FEATURE:
<221> NAME/KEY: misc_feature
<223> OTHER INFORMATION: Incyte ID No: 2903046F6
<221> NAME/KEY: unsure
<222> LOCATION: 4, 14, 123, 362
<223> OTHER INFORMATION: a, t, c, g, or other

<400> SEQUENCE: 8

```
ggcnggtcta agangagcag tgacccgtcc ccggcagggg acaatgagat tgagcgtgtg    60
ttcgtgtggg acttggatga gacaataatt attttttcact ccttactcac ggggacatt    120 gcntccagat acgggaagga caccacgacg tccgtgcgca ttggccttat gatggaagag   180
atgatcttca accttgcaga tacacatctg ttcttcaatg acctggagga ttgtgaccag   240
atccacgttg atgacgtctc atcagatgac aatggccaag atttaagcac atacaacttc   300
tccgctgacg gcttccacag ttcggcccca ggagccaacc tgtgcctggg tctggcgtgc   360
anggcggcgt gggactggat gaggaa                                        386
```

<210> SEQ ID NO 9
<211> LENGTH: 347
<212> TYPE: DNA
<213> ORGANISM: Homo sapiens
<220> FEATURE:
<221> NAME/KEY: misc_feature
<223> OTHER INFORMATION: Incyte ID No: 2328022R6

<400> SEQUENCE: 9

```
attttgccga aatatgagaa ctggggcctc ctgctcccag ggagctccag ggcccctctc    60
tcctcccacc tggacttggg gggaactgag aaacactttc ctggagctgc tggcttttgc   120
acttttttga tggcagaagt gtgacctgag agtcccacct tctcttcagg aacgtagatg   180 ttgggggtgtc ttgccctggg gggcttggaa cctctgaagg tggggagcgg aacacctggc   240
atccttcccc agcacttgca ttaccgtccc tgctcttccc aggtgggga cagtgggcca    300
```

```
agcaaaggct tcaacttcgg cagccaattt ctttcaaaga agcttgc                    347

<210> SEQ ID NO 10
<211> LENGTH: 371
<212> TYPE: DNA
<213> ORGANISM: Homo sapiens
<220> FEATURE:
<221> NAME/KEY: misc_feature
<223> OTHER INFORMATION: Incyte ID No: 2543603F7
<221> NAME/KEY: unsure
<222> LOCATION: 211, 231, 242, 256, 260, 267, 284, 303, 307, 339, 365
<223> OTHER INFORMATION: a, t, c, g, or other

<400> SEQUENCE: 10
ctgctctaac aatcaatggt acaggcccgg caactgactg gctgtctgct gaaacttttg      60
aaagtgacct agatgaaact cgtgttccta gaagtgccta gctctcttca cgtacgcccg     120
ctcgttacta gcatcgtagt gagctggact cctccagaga atcagaacat tgtggtcaga     180
ggttacgcca ttggttatgg cattggcagc nctcatgccc agaccatcaa nagtggacta     240
tnaacagcgc tattanaccn ttgaaantct ggatcccagc tctnactatg tgattaccct     300
ganagcnttt aataacgtgg gtgaaggcat ccccctgtnt gaagagtgct gtgaccaggc     360
ctcanacagt g                                                          371

<210> SEQ ID NO 11
<211> LENGTH: 514
<212> TYPE: DNA
<213> ORGANISM: Homo sapiens
<220> FEATURE:
<221> NAME/KEY: misc_feature
<223> OTHER INFORMATION: Incyte ID No: 1662856F6
<221> NAME/KEY: unsure
<222> LOCATION: 92, 445, 473, 491, 500
<223> OTHER INFORMATION: a, t, c, g, or other

<400> SEQUENCE: 11
ctggaattca ccaaggtttg ttggagactg aaccgttgca aggaacagac gaagatgcag      60
tagccagtgc tgacttctct agcatgctct cngaggagga aaaggaagag ttaaaagcag     120
agttagttca gctagaagac gaaattacaa cactacgaca agttttgtca gcgaaagaaa     180
ggcatctagt tgagataaaa caaaaactcg gcatgaacct gatgaatgaa ttaaaacaga     240
acttcagcaa aagctggcat gacatgcaga ctaccactgc ctacaagaaa acacatgaaa     300
ccctgagtca cgcagggcaa aaggcaactg cagctttcag caacgttgga acggccatca     360
gcaagaagtt cggagacatg agacgaaagt aggcggtacg aaccctaatg gaggcagttt     420
tgaggaggtc ctcagctcca cgggnccatt gccagtgccc cagagcttgg cangaaggct     480
ccccggcgga nccaagggan ggagggagcc tgcc                                 514

<210> SEQ ID NO 12
<211> LENGTH: 370
<212> TYPE: DNA
<213> ORGANISM: Homo sapiens
<220> FEATURE:
<221> NAME/KEY: misc_feature
<223> OTHER INFORMATION: Incyte ID No: 1553168F6
<221> NAME/KEY: unsure
<222> LOCATION: 50
<223> OTHER INFORMATION: a, t, c, g, or other

<400> SEQUENCE: 12
aagggatcaa actgtttcca agtaacataa agtctaagaa gatttatggn aatccagaaa      60
tacccagcac ccaacaagtt aagattcaca atgtctagca ttcagtcaaa gatgaccaag     120
```

```
tgtgcaaaga agtgagaaaa cgacctctaa caagaataat cagttgagac caaactgtag      180
cttaaataga tactagaatt agcagacaag gacattaaaa cagttataac tgctttccct      240
atgtttaaaa agttaactac ggacatagaa gatacttta aaagtcccaa atcaaactta      300
gagagttgaa aactataatc cctgagacga aaaatatact ggatgggatt aatggtagat      360
tgcaccttgt                                                             370
```

<210> SEQ ID NO 13
<211> LENGTH: 402
<212> TYPE: DNA
<213> ORGANISM: Homo sapiens
<220> FEATURE:
<221> NAME/KEY: misc_feature
<223> OTHER INFORMATION: Incyte ID No: 1984629R6

<400> SEQUENCE: 13

```
gtgttgccag ttgattgatg actgggagcc aaagtggcat ctcctttgac ctaaacgggc       60
gatgatgaaa taaaactcaa cagcctttct ctcatcttgc attgtgagat gcgaaataga      120
gcgtgtctct ctgcctctca ttttaggctg aggccgtcca aagcggccat gccccatgtt      180
tccactagat ggcgctgaca cttcaggcat caaccctcat ggcctctcag ccttgcaaag      240
gcagccactt aaagtcggtg tcctgtgtgg ggcaccaagc tgagctgcag acacccagta      300
ggcgcgaggc aaatgcgtcc cattttaaga ggcttgtatt tatgagctct ttgcttcctc      360
cctcccacta tctttaaaga attgctctcc atctcctttg gg                         402
```

<210> SEQ ID NO 14
<211> LENGTH: 319
<212> TYPE: DNA
<213> ORGANISM: Homo sapiens
<220> FEATURE:
<221> NAME/KEY: misc_feature
<223> OTHER INFORMATION: Incyte ID No: 2232320F6

<400> SEQUENCE: 14

```
tttgaatgtt ctcatccctt ttgcagcttt tcttttggc tctctcatgt ccttggcttg       60
ctcctctatt ctacctctct ttctccagca ataatatgca aatgaagaca tgtatccata      120
agaaggagtg ctcttcatca actaatagag cacctaccac agtgtcatac ctggtagagg      180
tgagcaattc atattcaaag gttgcaaagt gtttgtaata tattcatgag gctggaagta      240
agaagaatta aaaatttgtc ctaattacaa tgagaaccat tctaggtagt gatcttggag      300
cacacatgaa taacttctg                                                   319
```

<210> SEQ ID NO 15
<211> LENGTH: 292
<212> TYPE: DNA
<213> ORGANISM: Homo sapiens
<220> FEATURE:
<221> NAME/KEY: misc_feature
<223> OTHER INFORMATION: Incyte ID No: 2880737H1

<400> SEQUENCE: 15

```
aaagaagaac gcctgtccat cgccttttta taagtccttc tctccacacc taaaagcagc       60
tgcagctgga agggcacaaa ttccactgtg taaaataaaa tattaggggc aacacacttc      120
atcaaggcag caggaatgag agagagcaga gaagatcaag gatgaagtct tgggtactga      180
aaaattcagt gctgggcaga aaaactgaca ggcagtacaa gtaacaaaca gaatccaagt      240
gggctggccc ttgtgcacag agctccaggt gacctctgga gagacatggg ca              292
```

<210> SEQ ID NO 16
<211> LENGTH: 470
<212> TYPE: DNA
<213> ORGANISM: Homo sapiens
<220> FEATURE:
<221> NAME/KEY: misc_feature
<223> OTHER INFORMATION: Incyte ID No: 3128876F6
<221> NAME/KEY: unsure
<222> LOCATION: 49
<223> OTHER INFORMATION: a, t, c, g, or other

<400> SEQUENCE: 16

```
ctcaggcaca attgtcacca aggagttaaa agcttcttct tcaatagang aattgttctg      60
ggggtcctgg agacttacca ttgagccatg caatctggga agcacaggaa taagtagaca     120
ctttgaaaat ggatttgaat gttctcatcc cttttgcagc ttttcttttt ggctctctca     180
tgtccttggc ttgctcctct attctacctc tctttctcca gcaataatat gcaaatgaag     240
acatgtatcc ataagaagga gtgctcttca tcaactaata gagcacctac cacagtgtca     300
tacctggtag aggtgagcaa ttcatattca aaggttgcaa agtgtttgta atatattcat     360
gaggctggaa gtaagaagaa ttaaaaattt gtcctaatta caatggagaa ccattctagg     420
tagtgatctt ggagcacaca tgaataactt tctgaaggtg caaccaaatc                470
```

DETECTION OF GENES REGULATED BY EGF IN BREAST CANCER

This application claims the benefit of U.S. Provisional Application No. 60/152,548 our Docket No. PA-0018 P, filed on Sep. 3, 1999.

FIELD OF THE INVENTION

The present invention relates to a composition comprising a plurality of polynucleotide probes which may be used in detecting expression of genes modulated in response to EGF, and which are associated with breast cancer.

BACKGROUND OF THE INVENTION

Intercellular communication is essential for the development and survival of multicellular organisms. Communication is achieved through the secretion of proteins by signaling cells and the internalization of these proteins by target cells. Growth factors are secreted proteins that mediate communication between signaling and target cells. The secreted growth factors bind to specific receptors on the surfaces of target cells, and bound receptors trigger second messenger signal transduction pathways. These signal transduction pathways elicit specific cellular responses in the target cells. Such responses can include the modulation of gene expression and the stimulation or inhibition of cell division, cell differentiation, and cell motility.

Epidermal growth factor (EGF) is a member of a broad class of polypeptide growth factors that generally act as mitogens in diverse cell types to stimulate wound healing, bone synthesis and remodeling, extracellular matrix synthesis, and proliferation of epithelial, epidermal, and connective tissues. In addition, EGF produces non-mitogenic effects in certain tissues. The EGF receptor (EGFR), and its stimulation by EGF, has been linked with a number of cell proliferative disorders or malignancies. These include skin hyperplasia, erythroblastosis, and fibrosarcoma in animals; and in humans, benign hyperplasia of the skin, mammary carcinoma, glioblastoma, and hepatic carcinoma. Other epithelial carcinomas associated with EGFR activity include prostatic hyperplasia/cancer, renal carcinoma, bladder cancer, laryngeal cancer, esophageal tumors, stomach cancer, colon carcinoma, ovarian adenomas, and lung cancer (Khazaie, K. et al. (1993) Cancer and Metastasis Rev. 12:255–274).

The relationship of EGFR expression to human mammary carcinoma has been particularly well studied. (See Khazaie et al., supra, and references cited therein for a review of this area.) Overexpression of EGFR, particularly coupled with down-regulation of the estrogen receptor (ER), has been a marker of poor prognosis in breast cancer patients. In addition, EGFR expression in breast tumor metastases is frequently elevated relative to the primary tumor, suggesting that EGFR is involved in tumor progression and metastasis. This is supported by accumulating evidence that EGF has pleiotropic effects on cell motility, chemotaxis, secretion and differentiation; cell functions related to metastatic potential. For example, EGF has been found to influence the expression and organization of integrins, a family of receptors known to function in cell attachment to the extracelluar matrix during metastasis (Nicolson, G. L. (1984) Expl. Cell Res. 150:3–22; Schirrmacher, V (1985) Adv. Cancer Res. 43:1–73). EGFR may influence cell-cell adhesion by affecting changes in the phosphorylation of certain proteins involved in the process, such as β-atenin, fodrin, spectrin, and tubulin (Khazaie et al., supra). EGF has also been shown to affect the production and release of various proteinases involved in cell invasion of the extracelluar matrix, such as metalloproteinases, aminopeptidases, serine proteases, cysteine proteases and aspartic proteinases, as well as proteinase inhibitors such as plasminogen activator inhibitor (PAI-1) and tissue inhibitors of metalloproteases (TIMP).

In addition to the various proteins indicated above that are affected by EGF activity, the EGF signal transduction pathway itself involves the recruitment and activation of a variety of molecules including phospholipase C, phosphoinositol-3 kinase, MAP kinase, raf kinase, and a GTPase-activating protein (GAP). The expression of these and other molecules effected by EGF activity may be useful for the prediction or monitoring of cell proliferative disorders, pre-malignant conditions, or the presence and progression of malignant diseases in which EGF participates.

Array technology can provide a simple way to explore the expression of a single polymorphic gene or a large number of related or unrelated genes. When the expression of a single gene is explored, arrays are employed to detect the expression of specific gene variants. For example, a p53 tumor suppressor gene array is used to determine whether individuals are carrying mutations that predispose them to cancer. The array has over tens of thousands of DNA probes to analyze more than 400 distinct mutations of p53.

DNA-based array technology is especially relevant for the rapid screening of expression of a large number of genes. There is a growing awareness that gene expression is affected in a global fashion. A genetic predisposition, disease or therapeutic treatment may affect, directly or indirectly, the expression of a large number of genes. In some cases the interactions may be expected, such as where the genes are part of the same signaling pathway. In other cases, the interactions may be totally unexpected, such as when the genes participate in separate signaling pathways. Therefore, DNA-based arrays can be used to investigate how genetic predisposition, disease, or therapeutic treatment affects the expression of a large number of genes.

The potential application of gene expression profiling to breast cancer is particularly relevant to improving diagnosis and prognosis of this disease. The mortality rate for breast cancer approaches 10% of all deaths in females between the ages of 45–54 (K. Gish (1999) AWIS Magazine, 28:7–10). However the survival rate based on early diagnosis of localized breast cancer is extremely high (97%), compared with the advanced stage of the disease in which the tumor has spread beyond the breast (22%). Current procedures for clinical breast examination are, however, lacking in sensitivity and specificity, and efforts are underway in other laboratories to develop comprehensive gene expression profiles for breast cancer that may be used in conjunction with conventional screening methods to improve diagnosis and prognosis of this disease (Gish, supra).

It would be advantageous to prepare DNA-based arrays that can be used for monitoring expression of a large number of genes associated with cell proliferative disorders and with pre-malignant and malignant conditions. The present invention provides for a composition comprising a plurality of polynucleotide probes for use in detecting changes in expression of a large number of genes encoding proteins associated with EGFR expression and activity. Such a microarray can be employed for diagnosis and monitoring of the treatment of any disease or precondition where EGFR activation is involved, in particular, breast cancer.

SUMMARY

The present invention provides a combination comprising a plurality of cDNAs, wherein each of the cDNAs comprises at least a fragment of a polynucleotide sequence or a complement thereof whose expression is modulated by EGF and is associated with breast cancer and which are selected from SEQ ID NOs: 1–16 as presented in the Sequence Listing. In one aspect, the combination is immobilized on a substrate.

The invention also provides a high throughput method to detect differential expression of one or more of the cDNAs of the combination. The method comprises hybridizing the substrate comprising the combination with the nucleic acids of a sample, thereby forming one or more hybridization complexes, detecting the hybridization complexes, and comparing the hybridization complexes with those of a standard, wherein differences in the size and signal intensity of each hybridization complex indicates differential expression of nucleic acids in the sample.

The invention further provides a high throughput method of screening a library or a plurality of molecules or compounds to identify a ligand. The method comprises combining the substrate comprising the combination with a library or a plurality of molecules or compounds under conditions to allow specific binding and detecting specific binding, thereby identifying a ligand. The library or a plurality of molecules or compounds are selected from DNA molecules, RNA molecules, peptide nucleic acid molecules, mimetics, peptides, transcription factors, repressors, and other regulatory proteins.

The invention still further provides an isolated cDNA selected from SEQ ID NOs: 12–16 as presented in the Sequence Listing. The invention still further provides a pharmaceutical composition comprising the cDNA and a suitable pharmaceutical carrier. The invention also provides a vector comprising the cDNA, a host cell comprising the vector, and a method for producing a protein comprising culturing the host cell under conditions for the expression of a protein and recovering the protein from the host cell culture. The invention additionally provides a method for purifying a ligand, the method comprising combining a cDNA of the invention with a sample under conditions which allow specific binding, recovering the bound cDNA, and separating the cDNA from the ligand, thereby obtaining purified ligand.

The present invention provides a purified protein encoded and produced by a cDNA of the invention. The invention also provides a high-throughput method for using a protein to screen a library or a plurality of molecules or compounds to identify a ligand. The method comprises combining the protein or a portion thereof with the library or a plurality of molecules or compounds under conditions to allow specific binding and detecting specific binding, thereby identifying a ligand which specifically binds the protein. A library or a plurality of molecules or compounds are selected from DNA molecules, RNA molecules, peptide nucleic acid molecules, mimetics, peptides, proteins, agonists, antagonists, antibodies or their fragments, immunoglobulins, inhibitors, drug compounds, and pharmaceutical agents. The invention further provides for using a protein to purify a ligand. The method comprises combining the protein or a portion thereof with a sample under conditions to allow specific binding, recovering the bound protein, and separating the protein from the ligand, thereby obtaining purified ligand. The invention yet still further provides a method for using the protein to produce an antibody. The method comprises immunizing an animal with the protein or an antigenically-effective epitope under conditions to elicit an antibody response, isolating animal antibodies, and screening the isolated antibodies with the protein to identify an antibody which specifically binds the protein. The invention yet still further provides a method for using the protein to purify antibodies which bind specifically to the protein.

DESCRIPTION OF THE SEQUENCE LISTING AND TABLES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing is a compilation of nucleic acid sequences obtained by sequencing clone inserts (isolates) of different cDNAs. Each sequence is identified by a sequence identification number (SEQ ID NO) and by the clone number from which it was obtained.

Table 1 lists genes differentially expressed in human BT20 breast carcinoma cells and in primary breast carcinoma tissue. In each page, the table contains (by column): 1) SEQ ID NO: as shown in the Sequence Listing; 2) the Genbank ID and; 3) gene description to which the Incyte sequence was annotated; 4–10) the differential expression of the gene in each of seven breast carcinoma tissue samples, and 5) the maximal differential expression of the gene measured during the time course of the experiment for BT20 cells.

DESCRIPTION OF THE INVENTION

Definitions

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a nucleic acid molecule of the Sequence Listing refers to a cDNA which is completely complementary over the full length of the sequence and which will hybridize to the nucleic acid molecule under conditions of high stringency.

A "combination" comprises at least two and up to 16 sequences selected from the group consisting of SEQ ID NOs: 1–16 as presented in the Sequence Listing.

"cDNA" refers to a chain of nucleotides, an isolated polynucleotide, nucleic acid molecule, or any fragment or complement thereof. It may have originated recombinantly or synthetically, be double-stranded or single-stranded, coding and/or noncoding, and purified or combined with carbohydrate, lipids, protein or inorganic elements or substances. Preferably, the cDNA is from about 4000 to about 5000 nucleotides.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403410) which provides identity within the conserved region. Brenner et al. (1998; Proc Natl Acad Sci 95:6073–6078) who analyzed BLAST for its ability to identify structural homologs by sequence identity found 30% identity is a reliable threshold for sequence alignments of at least 150 residues and 40% is a reasonable threshold for alignments of at least 70 residues (Brenner et al., page 6076, column 2).

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid molecule in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein retains at least one biological or antigenic characteristic of a native protein. An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid.

The Invention

The present invention provides a combination comprising a plurality of polynucleotide probes, comprising at least a fragment of a gene whose transcript is modulated in response to EGF. Preferably, the plurality of probes comprise at least a fragment of one or more of the sequences, SEQ ID NOs: 1–16, presented in the Sequence Listing; and they are arranged on a substrate, preferably a microarray.

The microarray can be used for large scale genetic or gene expression analysis of a large number of targets. The microarray can also be used in the diagnosis of diseases and in the monitoring of treatments where altered expression of genes is associated with a cell proliferative disorder, in particular, breast cancer. Further, the microarray can be employed to investigate an individual's predisposition to a disease, in particular, breast cancer.

In a preferred embodiment, the combination provides the expression of those probes selected from SEQ ID NOs: 1–16 which are associated with breast cancer When the composition of the invention is employed as hybridizable elements in a microarray, the elements are organized in an ordered fashion so that each element is present at a specified location on the substrate. Because the elements are at specified locations on the substrate, the hybridization patterns and intensities, which together create a unique expression profile, can be interpreted in terms of expression levels of particular genes and can be correlated with a particular metabolic process, condition, disorder, disease, stage of disease, or treatment.

The combination comprising a plurality of cDNAs can also be used to identify or purify a molecule or compound which specifically binds to at least one of the cDNAs. These molecules may be identified from a sample or in high throughput mode from a library of mRNAs, cDNAs, genomic fragments, and the like. Typically, samples or libraries will include targets of diagnostic or therapeutic interest. If nucleic acids in a particular sample enhance the hybridization background, it may be advantageous to remove these nucleic acids. One method for removing additional nucleic acids is by hybridizing the sample with immobilized probes and washing away those nucleic acids that do not form hybridization complexes. At a later point, hybridization complexes can be dissociated, thereby releasing the purified targets.

cDNAs and Their Uses cDNAs can be prepared by a variety of synthetic or enzymatic methods well known in the art. cDNAs can be synthesized, in whole or in part, using chemical methods well known in the art (Caruthers et al. (1980) Nucleic Acids Symp. Ser. (7)215–233). Alternatively, cDNAs can be produced enzymatically or recombinantly, by in vitro or in vivo transcription.

Nucleotide analogs can be incorporated into cDNAs by methods well known in the art. The only requirement is that the incorporated analog must base pair with native purines or pyrimidines. For example, 2, 6-diaminopurine can substitute for adenine and form stronger bonds with thymidine than those between adenine and thymidine. A weaker pair is formed when hypoxanthine is substituted for guanine and base pairs with cytosine. Additionally, cDNAs can include nucleotides that have been derivatized chemically or enzymatically.

cDNAs can be synthesized on a substrate. Synthesis on the surface of a substrate may be accomplished using a chemical coupling procedure and a piezoelectric printing apparatus as described by Baldeschweiler et al. (PCT publication WO95/251116). Alternatively, the cDNAs can be synthesized on a substrate surface using a self-addressable electronic device that controls when reagents are added as described by Heller et al. (U.S. Pat. No. 5,605,662). cDNAs can be synthesized directly on a substrate by sequentially dispensing reagents for their synthesis on the substrate surface or by dispensing preformed DNA fragments to the substrate surface. Typical dispensers include a micropipette delivering solution to the substrate with a robotic system to control the position of the micropipette with respect to the substrate. There can be a multiplicity of dispensers so that reagents can be delivered to the reaction regions efficiently.

cDNAs can be immobilized on a substrate by covalent means such as by chemical bonding procedures or UV irradiation. In one method, a cDNA is bound to a glass surface which has been modified to contain epoxide or aldehyde groups. In another method, a cDNA is placed on a polylysine coated surface and UV cross-linked to it as described by Shalon et al. (WO95/35505). In yet another method, a cDNA is actively transported from a solution to a given position on a substrate by electrical means (Heller, supra). cDNAs do not have to be directly bound to the substrate, but rather can be bound to the substrate through a linker group. The linker groups are typically about 6 to 50 atoms long to provide exposure of the attached cDNA. Preferred linker groups include ethylene glycol oligomers, diamines, diacids and the like. Reactive groups on the substrate surface react with a terminal group of the linker to bind the linker to the substrate. The other terminus of the linker is then bound to the cDNA. Alternatively, polynucleotides, plasmids or cells can be arranged on a filter. In the latter case, cells are lysed, proteins and cellular components degraded, and the DNA is coupled to the filter by UV cross-linking.

The cDNAs may be used for a variety of purposes. For example, the combination of the invention may be used on an array. The array, in turn, can be used in high-throughput methods for detecting a related polynucleotide in a sample, screening a plurality of molecules or compounds to identify a ligand, diagnosing a breast cancer, or inhibiting or inactivating a therapeutically relevant gene related to the cDNA.

When the cDNAs of the invention are employed on a microarray, the cDNAs are arranged in an ordered fashion so that each cDNA is present at a specified location. Because the cDNAs are at specified locations on the substrate, the hybridization patterns and intensities, which together create a unique expression profile, can be interpreted in terms of expression levels of particular genes and can be correlated with a particular metabolic process, condition, disorder, disease, stage of disease, or treatment.

*Hybridization*

The cDNAs or fragments or complements thereof may be used in various hybridization technologies. The cDNAs may be labeled using a variety of reporter molecules by either PCR, recombinant, or enzymatic techniques. For example, a commercially available vector containing the cDNA is transcribed in the presence of an appropriate polymerase, such as T7 or SP6 polymerase, and at least one labeled nucleotide. Commercial kits are available for labeling and cleanup of such cDNAs. Radioactive (Amersham Pharmacia Biotech (APB), Piscataway N.J.), fluorescent (Operon Technologies, Alameda Calif.), and chemiluminescent labeling (Promega, Madison Wis.) are well known in the art.

A cDNA may represent the complete coding region of an mRNA or be designed or derived from unique regions of the mRNA or genomic molecule, an intron, a 3' untranslated region, or from a conserved motif. The cDNA is at least 18 contiguous nucleotides in length and is usually single stranded. Such a cDNA may be used under hybridization conditions that allow binding only to an identical sequence, a naturally occurring molecule encoding the same protein, or an allelic variant. Discovery of related human and mammalian sequences may also be accomplished using a pool of degenerate cDNAs and appropriate hybridization conditions. Generally, a cDNA for use in Southern or northern hybridizations may be from about 400 to about 6000 nucleotides long. Such cDNAs have high binding specificity in solution-based or substrate-based hybridizations. An oligonucleotide, a fragment of the cDNA, may be used to detect a polynucleotide in a sample using PCR.

The stringency of hybridization is determined by G+C content of the cDNA, salt concentration, and temperature. In particular, stringency is increased by reducing the concentration of salt or raising the hybridization temperature. In solutions used for some membrane based hybridizations, addition of an organic solvent such as formamide allows the reaction to occur at a lower temperature. Hybridization may be performed with buffers, such as 5× saline sodium citrate (SSC) with 1% sodium dodecyl sulfate (SDS) at 60° C., that permit the formation of a hybridization complex between nucleic acid sequences that contain some mismatches. Subsequent washes are performed with buffers such as 0.2×SSC with 0.1% SDS at either 45° C. (medium stringency) or 65°–68° C. (high stringency). At high stringency, hybridization complexes will remain stable only where the nucleic acid molecules are completely complementary. In some membrane-based hybridizations, preferably 35% or most preferably 50%, formamide may be added to the hybridization solution to reduce the temperature at which hybridization is performed. Background signals may be reduced by the use of detergents such as Sarkosyl or Triton X-100 (Sigma Aldrich, St. Louis Mo.) and a blocking agent such as denatured salmon sperm DNA. Selection of components and conditions for hybridization are well known to those skilled in the art and are reviewed in Ausubel et al. (1997, *Short Protocols in Molecular Biology*, John Wiley & Sons, New York N.Y., Units 2.8–2.11, 3.18–3.19 and 4–64.9).

Dot-blot, slot-blot, low density and high density arrays are prepared and analyzed using methods known in the art. cDNAs from about 18 consecutive nucleotides to about 5000 consecutive nucleotides in length are contemplated by the invention and used in array technologies. The preferred number of cDNAs on an array is at least about 100,000, a more preferred number is at least about 40,000, an even more preferred number is at least about 10,000, and a most preferred number is at least about 600 to about 800. The array may be used to monitor the expression level of large numbers of genes simultaneously and to identify genetic variants, mutations, and SNPs. Such information may be used to determine gene function; to understand the genetic basis of a disorder; to diagnose a disorder; and to develop and monitor the activities of therapeutic agents being used to control or cure a disorder. (See, e.g., U.S. Pat. No. 5,474,796; WO95/11995; WO95/35505; U.S. Pat. No. 5,605,662; and U.S. Pat. No. 5,958,342.)

Screening and Purification Assays

A cDNA may be used to screen a library or a plurality of molecules or compounds for a ligand which specifically binds the cDNA. Ligands may be DNA molecules, RNA molecules, peptide nucleic acid molecules, peptides, proteins such as transcription factors, promoters, enhancers, repressors, and other proteins that regulate replication, transcription, or translation of the polynucleotide in the biological system. The assay involves combining the cDNA or a fragment thereof with the molecules or compounds under conditions that allow specific binding and detecting the bound cDNA to identify at least one ligand that specifically binds the cDNA.

In one embodiment, the cDNA may be incubated with a library of isolated and purified molecules or compounds and binding activity determined by methods such as a gel-retardation assay (U.S Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay. Protein binding may be confirmed by raising antibodies against the protein and adding the antibodies to the gel-retardation assay where specific binding will cause a supershift in the assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

The cDNA may be used to purify a ligand from a sample. A method for using a cDNA to purify a ligand would involve combining the cDNA or a fragment thereof with a sample under conditions to allow specific binding, recovering the bound cDNA, and using an appropriate agent to separate the cDNA from the purified ligand.

Protein Production and Uses

The full length cDNAs or fragment thereof may be used to produce purified proteins using recombinant DNA technologies described herein and taught in Ausubel et al. (supra; Units 16.1–16.62). One of the advantages of producing proteins by these procedures is the ability to obtain highly-enriched sources of the proteins thereby simplifying purification procedures.

The proteins may contain amino acid substitutions, deletions or insertions made on the basis of similarity in polarity, charge, solubility, hydrophobicity, hydrophilicity, and/or the amphipathic nature of the residues involved. Such substitutions may be conservative in nature when the substituted residue has structural or chemical properties similar to the original residue (e.g., replacement of leucine with isoleucine or valine) or they may be nonconservative when the replacement residue is radically different (e.g., a glycine replaced by a tryptophan). Computer programs included in LASERGENE software (DNASTAR, Madison Wis.), MACVECTOR software (Genetics Computer Group, Madison Wis.) and RasMol software (www.umass.edu/microbio/rasmol) may be used to help determine which and how many amino acid residues in a particular portion of the protein may be substituted, inserted, or deleted without abolishing biological or immunological activity.

Expression of Encoded Proteins

Expression of a particular cDNA may be accomplished by cloning the cDNA into a vector and transforming this vector into a host cell. The cloning vector used for the construction of cDNA libraries in the LIFESEQ databases may also be used for expression. Such vectors usually contain a promoter and a polylinker useful for cloning, priming, and transcription. An exemplary vector may also contain the promoter for β-galactosidase, an amino-terminal methionine and the subsequent seven amino acid residues of β-galactosidase. The vector may be transformed into competent *E. coli* cells. Induction of the isolated bacterial strain with isopropylthiogalactoside (IPTG) using standard methods will produce a fusion protein that contains an N terminal methionine, the first seven residues of β-galactosidase, about 15 residues of linker, and the protein encoded by the cDNA.

The cDNA may be shuttled into other vectors known to be useful for expression of protein in specific hosts. Oligonucleotides containing cloning sites and fragments of DNA sufficient to hybridize to stretches at both ends of the cDNA may be chemically synthesized by standard methods. These primers may then be used to amplify the desired fragments by PCR. The fragments may be digested with appropriate restriction enzymes under standard conditions and isolated using gel electrophoresis. Alternatively, similar fragments are produced by digestion of the cDNA with appropriate restriction enzymes and filled in with chemically synthesized oligonucleotides. Fragments of the coding sequence from more than one gene may be ligated together and expressed.

Signal sequences that dictate secretion of soluble proteins are particularly desirable as component parts of a recombinant sequence. For example, a chimeric protein may be expressed that includes one or more additional purification-facilitating domains. Such domains include, but are not limited to, metal-chelating domains that allow purification on immobilized metals, protein A domains that allow purification on immobilized immunoglobulin, and the domain utilized in the FLAGS extension/affinity purification system (Immunex, Seattle Wash.). The inclusion of a cleavable-linker sequence such as ENTEROKINASEMAX (Invitrogen, San Diego Calif.) between the protein and the purification domain may also be used to recover the protein.

Suitable host cells may include, but are not limited to, mammalian cells such as Chinese Hamster Ovary (CHO) and human 293 cells, insect cells such as Sf9 cells, plant cells such as *Nicotiana tabacum*, yeast cells such as *Saccharomyces cerevisiae*, and bacteria such as *E. coli*. For each of these cell systems, a useful vector may also include an origin of replication and one or two selectable markers to allow selection in bacteria as well as in a transformed eukaryotic host. Vectors for use in eukaryotic host cells may require the addition of 3' poly(A) tail if the cDNA lacks poly(A).

Additionally, the vector may contain promoters or enhancers that increase gene expression. Many promoters are known and used in the art. Most promoters are host specific and exemplary promoters includes SV40 promoters for CHO cells; T7 promoters for bacterial hosts; viral promoters and enhancers for plant cells; and PGH promoters for yeast. Adenoviral vectors with the rous sarcoma virus enhancer or retroviral vectors with long terminal repeat promoters may be used to drive protein expression in mammalian cell lines. Once homogeneous cultures of recombinant cells are obtained, large quantities of secreted soluble protein may be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, and the like.

In addition to recombinant production, proteins or portions thereof may be produced manually, using solid-phase techniques (Stewart et al. (1969) *Solid-Phase Peptide Synthesis*, W H Freeman, San Francisco Calif.; Merrifield (1963) J Am Chem Soc 5:2149–2154), or using machines such as the ABI 431A peptide synthesizer (Applied Biosystems, Foster City Calif.). Proteins produced by any of the above methods may be used as pharmaceutical compositions to treat disorders associated with null or inadequate expression of the genomic sequence.

Screening and Purification Assays

A protein or a portion thereof encoded by the cDNA may be used to screen a library or a plurality of molecules or compounds for a ligand with specific binding affinity or to purify a molecule or compound from a sample. The protein or portion thereof employed in such screening may be free in solution, affixed to an abiotic or biotic substrate, or located intracellularly. For example, viable or fixed prokaryotic host cells that are stably transformed with recombinant nucleic acids that have expressed and positioned a protein on their cell surface can be used in screening assays. The cells are screened against a library or a plurality of ligands and the specificity of binding or formation of complexes between the expressed protein and the ligand may be measured. The ligands may be DNA, RNA, or PNA molecules, agonists, antagonists, antibodies, immunoglobulins, inhibitors, peptides, pharmaceutical agents, proteins, drugs, or any other test molecule or compound that specifically binds the protein. An exemplary assay involves combining the mammalian protein or a portion thereof with the molecules or compounds under conditions that allow specific binding and detecting the bound protein to identify at least one ligand that specifically binds the protein.

This invention also contemplates the use of competitive drug screening assays in which neutralizing antibodies capable of binding the protein specifically compete with a test compound capable of binding to the protein or oligopeptide or fragment thereof. One method for high throughput screening using very small assay volumes and very small amounts of test compound is described in U.S Pat. No. 5,876,946. Molecules or compounds identified by screening may be used in a model system to evaluate their toxicity, diagnostic, or therapeutic potential.

The protein may be used to purify a ligand from a sample. A method for using a protein to purify a ligand would involve combining the protein or a portion thereof with a sample under conditions to allow specific binding, recovering the bound protein, and using an appropriate chaotropic agent to separate the protein from the purified ligand.

Production of Antibodies

A protein encoded by a cDNA of the invention may be used to produce specific antibodies. Antibodies may be produced using an oligopeptide or a portion of the protein with inherent immunological activity. Methods for producing antibodies include: 1) injecting an animal, usually goats, rabbits, or mice, with the protein, or an antigenically-effective portion or an oligopeptide thereof, to induce an immune response; 2) engineering hybridomas to produce monoclonal antibodies; 3) inducing in vivo production in the lymphocyte population; or 4) screening libraries of recombinant immunoglobulins. Recombinant immunoglobulins may be produced as taught in U.S Pat. No. 4,816,567.

Antibodies produced using the proteins of the invention are useful for the diagnosis of prepathologic disorders as well as the diagnosis of chronic or acute diseases characterized by abnormalities in the expression, amount, or distribution of the protein. A variety of protocols for competitive binding or immunoradiometric assays using either polyclonal or monoclonal antibodies specific for proteins are well known in the art. Immunoassays typically involve the formation of complexes between a protein and its specific binding molecule or compound and the measurement of complex formation. Immunoassays may employ a two-site, monoclonal-based assay that utilizes monoclonal antibodies reactive to two noninterfering epitopes on a specific protein or a competitive binding assay (Pound (1998) *Immunochemical Protocols*, Humana Press, Totowa N.J.).

Immunoassay procedures may be used to quantify expression of the protein in cell cultures, in subjects with a particular disorder or in model animal systems under various conditions. Increased or decreased production of proteins as monitored by immunoassay may contribute to knowledge of the cellular activities associated with developmental pathways, engineered conditions or diseases, or treatment efficacy. The quantity of a given protein in a given tissue may be determined by performing immunoassays on freeze-thawed detergent extracts of biological samples and comparing the slope of the binding curves to binding curves generated by purified protein.

Labeling of Molecules for Assay

A wide variety of reporter molecules and conjugation techniques are known by those skilled in the art and may be used in various cDNA, polynucleotide, protein, peptide or antibody assays. Synthesis of labeled molecules may be achieved using commercial kits for incorporation of a labeled nucleotide such as $^{32}$P-dCTP, Cy3-dCTP or Cy5-dCTP or amino acid such as $^{35}$S-methionine. Polynucleotides, cDNAs, proteins, or antibodies may be directly labeled with a reporter molecule by chemical conjugation to amines, thiols and other groups present in the molecules using reagents such as BIODIPY or FITC (Molecular Probes, Eugene Oreg.).

The proteins and antibodies may be labeled for purposes of assay by joining them, either covalently or noncovalently, with a reporter molecule that provides for a detectable signal. A wide variety of labels and conjugation techniques are known and have been reported in the scientific and patent literature including, but not limited to U.S Pat. No. 3,817,837; 3,850,752; 3,939,350; 3,996,345; 4,277,437; 4,275,149; and 4,366,241.

DIAGNOSTICS

The cDNAs, or fragments thereof, may be used to detect and quantify differential gene expression; absence, presence, or excess expression of mRNAs; or to monitor mRNA levels during therapeutic intervention associated with breast cancer. These cDNAs can also be utilized as markers of treatment efficacy against breast cancer over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

For example, the cDNA may be labeled by standard methods and added to a biological sample from a patient under conditions for hybridization complex formation. After an incubation period, the sample is washed and the amount of label (or signal) associated with hybridization complexes is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Gene Expression Profiles

A gene expression profile comprises a plurality of cDNAs and a plurality of detectable hybridization complexes, wherein each complex is formed by hybridization of one or more probes to one or more complementary sequences in a sample. The cDNAs of the invention are used as elements on a microarray to analyze gene expression profiles. In one embodiment, the microarray is used to monitor the progression of disease. Researchers can assess and catalog the differences in gene expression between healthy and diseased tissues or cells. By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the microarray is employed to improve the treatment regimen. A dosage is established that causes a change in genetic expression patterns indicative of successful treatment. Expression patterns associated with the onset of undesirable side effects are avoided. This approach may be more sensitive and rapid than waiting for the patient to show inadequate improvement, or to manifest side effects, before altering the course of treatment.

In another embodiment, animal models which mimic a human disease can be used to characterize expression profiles associated with a particular condition, disorder or disease; or treatment of the condition, disorder or disease. Novel treatment regimens may be tested in these animal models using microarrays to establish and then follow expression profiles over time. In addition, microarrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Assays Using Antibodies

Antibodies directed against epitopes on a protein encoded by a cDNA of the invention may be used in assays to quantify the amount of protein found in a particular human cell. Such assays include methods utilizing the antibody and a label to detect expression level under normal or disease conditions. The antibodies may be used with or without modification, and labeled by joining them, either covalently or noncovalently, with a labeling moiety.

Protocols for detecting and measuring protein expression using either polyclonal or monoclonal antibodies are well known in the art. Examples include ELISA, RIA, and fluorescent activated cell sorting (FACS). Such immunoassays typically involve the formation of complexes between the protein and its specific antibody and the measurement of such complexes. These and other assays are described in Pound (supra). The method may employ a two-site, monoclonal-based immunoassay utilizing monoclonal antibodies reactive to two non-interfering epitopes, or a competitive binding assay. (See, e.g., Coligan et al. (1997) *Current Protocols in Immunology*, Wiley-Interscience, New York N.Y.; Pound, supra)

THERAPEUTICS

The cDNAs and fragments thereof can be used in gene therapy. cDNAs can be delivered ex vivo to target cells, such as cells of bone marrow. Once stable integration and transcription and or translation are confirmed, the bone marrow may be reintroduced into the subject. Expression of the protein encoded by the cDNA may correct a disorder associated with mutation of a normal sequence, reduction or loss of an endogenous target protein, or overexpression of an endogenous or mutant protein. Alternatively, cDNAs may be delivered in vivo using vectors such as retrovirus, adenovirus, adeno-associated virus, herpes simplex virus, and bacterial plasmids. Non-viral methods of gene delivery include cationic liposomes, polylysine conjugates, artificial viral envelopes, and direct injection of DNA (Anderson (1998) Nature 392:25–30; Dachs et al. (1997) Oncol Res 9:313–325; Chu et al. (1998) J Mol Med 76(3–4):184–192; Weiss et al. (1999) Cell Mol Life Sci 55(3):334–358; Agrawal (1996) *Antisense Therapeutics*, Humana Press, Totowa N.J.; and August et al. (1997) *Gene Therapy (Advances in Pharmacology*. Vol. 40), Academic Press, San Diego Calif.).

In addition, expression of a particular protein can be regulated through the specific binding of a fragment of a cDNA to a genomic sequence or an mRNA which encodes the protein or directs its transcription or translation. The cDNA can be modified or derivatized to any RNA-like or DNA-like material including peptide nucleic acids, branched nucleic acids, and the like. These sequences can be produced biologically by transforming an appropriate host cell with a vector containing the sequence of interest.

Molecules which regulate the activity of the cDNA or encoded protein are useful as therapeutics for breast cancer. Such molecules include agonists which increase the expression or activity of the polynucleotide or encoded protein, respectively; or antagonists which decrease expression or activity of the polynucleotide or encoded protein, respectively. In one aspect, an antibody which specifically binds the protein may be used directly as an antagonist or indirectly as a delivery mechanism for bringing a pharmaceutical agent to cells or tissues which express the protein.

Additionally, any of the proteins, or their ligands, or complementary nucleic acid sequences may be administered as pharmaceutical compositions or in combination with other appropriate therapeutic agents. Selection of the appropriate agents for use in combination therapy may be made by one of ordinary skill in the art, according to conventional pharmaceutical principles. The combination of therapeutic agents may act synergistically to affect the treatment or prevention of the conditions and disorders associated with EGF regulation. Using this approach, one may be able to achieve therapeutic efficacy with lower dosages of each agent, thus reducing the potential for adverse side effects. Further, the therapeutic agents may be combined with pharmaceutically-acceptable carriers including excipients and auxiliaries which facilitate processing of the active compounds into preparations which can be used pharmaceutically. Further details on techniques for formulation and administration used by doctors and pharmacists may be found in the latest edition of *Remington's Pharmaceutical Sciences* (Maack Publishing, Easton Pa.).

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of underexpression or overexpression of genes of interest and for the development of methods for diagnosis and treatment of diseases. A mammal inbred to overexpress a particular gene (for example, secreted in milk) may also serve as a convenient source of the protein expressed by that gene.

Transgenic Animal Models

Transgenic rodents that overexpress or underexpress a gene of interest may be inbred and used to model human diseases or to test therapeutic or toxic agents. (See, e.g., U.S Pat. No. 5,175,383 and U.S Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells such as the mouse 129/SvJ cell line are placed in a blastocyst from the C57BL/6 mouse strain, they resume normal development and contribute to tissues of the liveborn animal. ES cells are preferred for use in the creation of experimental knockout and knockin animals. The method for this process is well known in the art and the steps are: the cDNA is introduced into a vector, the vector is transformed into ES cells, transformed cells are identified and microinjected into mouse cell blastocysts, blastocysts are surgically transferred to pseudopregnant dams. The resulting chimeric progeny are genotyped and bred to produce heterozygous or homozygous strains.

Knockout Analysis

In gene knockout analysis, a region of a gene is enzymatically modified to include a non-natural intervening sequence such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene.

Knockin Analysis

ES cells can be used to create knockin humanized animals or transgenic animal models of human diseases. With knockin technology, a region of a human gene is injected into animal ES cells, and the human sequence integrates into the animal cell genome. Transgenic progeny or inbred lines are studied and treated with potential pharmaceutical agents to obtain information on the progression and treatment of the analogous human condition.

As described herein, the uses of the cDNAs, provided in the Sequence Listing of this application, and their encoded proteins are exemplary of known techniques and are not intended to reflect any limitation on their use in any technique that would be known to the person of average skill in the art. Furthermore, the cDNAs provided in this application may be used in molecular biology techniques that have not yet been developed, provided the new techniques rely on properties of nucleotide sequences that are currently known to the person of ordinary skill in the art, e.g., the triplet genetic code, specific base pair interactions, and the like.

Likewise, reference to a method may include combining more than one method for obtaining or assembling full length cDNA sequences that will be known to those skilled in the art. It is also to be understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

EXAMPLES

For purposes of example, the preparation and sequencing of the breast tissue cDNA library (BRSTNOT07), from which Incyte Clone 1297817 was identified is described. Preparation and sequencing of cDNAs in libraries in the LIFESEQ database (Incyte Genomics) have varied over time, and the gradual changes involved use of kits, plasmids, and machinery available at the particular time the library was made and analyzed.

I cDNA Library Preparation

The BRSTNOT07 cDNA library was constructed from diseased breast tissue removed from a 43-year-old Caucasian female during unilateral extended simple mastectomy. Pathology indicated mildly proliferative fibrocystic changes with epithelial hyperplasia, papillomatosis, and duct ectasia. Pathology for the matched tumor tissue indicated invasive grade 4, nuclear grade 3 mammary adenocarcinoma with extensive comedo necrosis.

The frozen tissue was homogenized and lysed in a guanidinium isothiocyanate solution using a POLYTRON homogenizer (PT-3000, Brinkmann Instruments, Westbury, N.J.). The lysate was centrifuged over a 5.7 M CsCl cushion using a SW28 rotor in an L8–70M ultracentrifuge (Beckman Instruments, Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. RNA extraction and precipitation was repeated as before. The mRNA was then isolated using the OLIGOTEX kit (Qiagen, Inc., Chatsworth, Calif.) and used to construct the cDNA library.

The mRNA was handled according to the recommended protocols in the SUPERSCRIPT plasmid System (Life Technologies). The cDNA were fractionated on a SEPHAROSE CL4B column (Amersham Pharmacia Biotech, Piscataway N.J.), and those cDNAs exceeding 400 bp were ligated into pSPORT I. The plasmid was subsequently transformed into DH5α competent cells (Life Technologies).

II Isolation and Sequencing of cDNA Clones

Plasmid DNA was released from the cells and purified using the REAL Prep 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cells were cultured for 19 hours and lysed with 0.3 ml of lysis buffer; and 3) following isopropanol precipitation, the DNA pellet was resuspended in 0.1 ml of distilled water. After the last step in the protocol, samples were transferred to a 96-well block for storage at 4° C.

The cDNAs were prepared using a MICROLAB 2200 system (Hamilton, Reno Nev.) in combination with DNA ENGINE thermal cyclers (PTC200; M J Research, Waltham Mass.). The cDNAs were sequenced by the method of Sanger and Coulson (1975; J. Mol. Biol. 94:441f) using ABI PRISM 377 DNA sequencing systems (PE Biosystems). Most of the sequences were sequenced using standard ABI protocols and kits (PE Biosystems) at solution volumes of 0.25×–1.0×. In the alternative, some of the sequences were sequenced using solutions and dyes from Amersham Pharmacia Biotech.

III Homology Searching of cDNA Clones and Their Deduced Proteins

As used herein, "homology" refers to sequence similarity between a reference sequence and at least a fragment of a newly sequenced clone insert, and can refer to either a nucleic acid or amino acid sequence. The GenBank databases which contain previously identified and annotated sequences, were searched for regions of homology using BLAST (Altschul (1993 and 1990) supra).

BLAST involves first finding similar segments between the query sequence and a database sequence, then evaluating the statistical significance of any matches that are found and finally reporting only those matches that satisfy a user-selectable threshold of significance. BLAST produces alignments of both nucleotide and amino acid sequences to determine sequence similarity. The fundamental unit of the BLAST algorithm output is the High scoring Segment Pair (HSP). An HSP consists of two sequence fragments of arbitrary, but equal lengths, whose alignment is locally maximal and for which the alignment score meets or exceeds a threshold or cutoff score set by the user.

The basis of the search is the product score, which is defined as:

$$\% \text{ sequence identity} \times \% \text{ maximum BLAST score}$$

The product score takes into account both the degree of identity between two sequences and the length of the sequence match as reflected in the BLAST score. The BLAST score is calculated by scoring +5 for every base that matches in an HSP and −4 for every mismatch. For example, with a product score of 40, the match will be exact within a 1% to 2% error, and, with a product score of 70, the match will be exact. Homologous molecules are usually identified by selecting those which show product scores between 15 and 40, although lower scores may identify related molecules. The P-value for any given HSP is a function of its expected frequency of occurrence and the number of HSPs observed against the same database sequence with scores at least as high. Percent sequence identity is found in a comparison of two or more amino acid or nucleic acid sequences. Percent identity can be determined electronically, e.g., by using the MEGALIGN program (DNASTAR). The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity.

Sequences with conserved protein motifs may also be searched using the BLOCKS search program. This program analyses sequence information contained in the Swiss-Prot Database and PROSITE and is useful for determining the classification of uncharacterized proteins translated from genomic or cDNA sequences (Bairoch, supra; Attwood, supra). PROSITE is a useful source for identifying functional or structural domains that are not detected using motifs due to extreme sequence divergence. Using weight matrices, these domains are calibrated against the SWISS-PROT database to obtain a measure of the chance distribution of the matches.

The PRINTS database can be searched using the BLIMPS search program to obtain protein family "fingerprints". The PRINTS database complements the PROSITE database by exploiting groups of conserved motifs within sequence alignments to build characteristic signatures of different protein families. For both BLOCKS and PRINTS analyses, the cutoff scores for local similarity were: >1300=strong, 1000–1300=suggestive; for global similarity were: p<exp–3; and for strength (degree of correlation) were: >1300=strong, 1000–1300=weak.

IV Extension of cDNA Clones

Some of the nucleic acid sequences of SEQ ID NO: 1–16 were produced by extension of an appropriate fragment of the molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer- primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the DNA Engine thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C. 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Step 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1× TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: Step 2, 3, and 4 repeated 29 times; Step 6: 72° C., 5 min; Step 7: storage at 4° C. DNA was quantifie by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (PE Biosystems).

V Propagation and Maintenance of Cultured Cells

The human breast carcinoma cell line (BT-20) was purchased from ATCC (Manassus, Va.); and primary mammary epithelial cells (HMEC), from Clonetics (San Diego, Calif.). The cells were propagated in media according to the supplier's recommendations.

VI Experimental Treatment of Cultured Cells

Cells were plated in culture dishes and grown at 37° C. in 5% $CO_2$ till 80% confluent. The cells were then grown for 48 hours in the presence of 1% fetal bovine serum (FBS), following which the spent media was removed and replaced with either media alone or media containing 50 ng/ml EGF (R and D system, Minneapolis, Minn.). Control and EGF-stimulated cells were lysed at different time points (e.g. 4, 8, 12, 24, 36, and 48 hours for the BT20 experiment) following treatment.

VII Preparation of mRNA

Following the experimental treatments described above, total RNA was extracted from cell samples using the TRI-ZOL reagent (Life Technologies) extraction protocol based on the supplier's recommendations, and the mRNA purified using the OLIGOTEX kit (Qiagen) described above.

The mRNA from four non-diseased breast tissue samples, prepared from three female patients ages 3242 and a pooled tissue sample from two donors ages 43 and 58, were obtained from BioChain Institute (San Leandro Calif.). mRNA from seven ductal carcinoma primary tumors, prepared from six female patients, ages 46–56, and one pool of 18 donors, ages 40–72, was also obtained from the same source.

VIII Labeling of Probes and Hybridization Analyses

Substrate Preparation

Target nucleic acids were amplified from bacterial vectors by thirty cycles of PCR using primers complementary to vector sequences flanking the insert. Amplified target nucleic acids were purified using SEPHACRYL-400 beads (Amersham Pharmacia Biotech). Purified target nucleic acids were robotically arrayed onto a glass microscope slide (Corning Science Products, Corning N.Y.). The slide was previously coated with 0.05% aminopropyl silane (Sigma-Aldrich, St. Louis Mo.) and cured at 110° C. The arrayed glass slide (microarray) was exposed to UV irradiation in a STRATALINKER V-crosslinker (Stratagene).

In an alternative method, a mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20× saline sodium citrate (SSC). Alternatively, targets are individually ligated to a vector and inserted into bacterial host cells to form a library. Target nucleic acids are arranged on substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

Probe Preparation

Each mRNA sample was reverse transcribed using MMLV reverse transcriptase in the presence of dCTP-Cy3 or dCTP-Cy5 (Amersham Pharmacia Biotech) according to standard protocol. After incubation at 37° C., the reaction was stopped with 0.5 M sodium hydroxide, and RNA was degraded at 85° C. The probes were then purified using Chroma Spin 30 gel filtration spin columns (Clontech, Palo Alto, Calif.) and ethanol precipitation.

Hybridization

Competitive hybridization was performed using RNA from (1) Control untreated versus EGF treated cells or (2) Normal breast versus tumor breast tissue.

The hybridization mixture, containing 0.2 mg of each of Cy3 and Cy5 labeled cDNA probes as starting material, was heated to 65 ° C., and added to the microarray surface. The array was covered with a coverslip and incubated at 60 ° C. The microarrays were washed at 45 ° C. in high stringency buffer (1×SSC and 0.1% SDS) followed by low stringency washes (0.1×SSC) and dried.

Detection

A laser microscope was used to detect the fluorescence-labeled probed. Excitation wavelengths were 488 nm for Cy3 and 632 nm for Cy5. Each array was scanned twice, one scan per fluorophore. The emission maxima was 565 nm for Cy3 and 650 nm for Cy5. The emitted light was split into two photomultiplier tube detectors based on wavelength. The output of the photomultiplier tube was digitized and displayed as an image, where the signal intensity was represented using a linear color transformation, with red representing a high signal and blue a low signal. The fluorescence signal for each element was integrated to obtain a numerical value corresponding to the signal intensity using GEMTOOLS gene expression analysis software (Incyte Genomics).

IX Data Analysis and Results

Data analysis using the GEMTOOLS gene expression analysis software (Incyte Genomics) was performed to identify those genes which exhibited a 2-fold or more change in expression in response to EGF and displayed a signal intensity of over 300. The sequences found in the Sequence Listing were selected because they showed at least a 2-fold change in expression in response to EGF treatment of a human breast tumor cell line, BT-20, and were also differentiatially expressed in primary breast carcinoma tissue samples. Comparisons of expression among these cells and tissues allowed the identification of genes potentially useful in diagnosing a breast cancer differentially expressed in BT20 cells and breast carcinoma tissue, but not in HMEC cells).

Table 1 lists genes differentially regulated by EGF treatment at least 2-fold in BT20 breast carcinoma cells that are also differentially regulated at least 2-fold in at least four of seven breast carcinoma tissue samples (BC). Column 1 lists the SEQ ID NO, column 2 the Genbank ID, and column 3 the description of the gene by BLAST, where identified. Sequences not identified by BLAST are indicated as "Incyte unique". Columns 4–10 list the differential expression of the gene in seven breast carcinoma tissue samples (BC1–BC7), and column 11 lists the maximal differential expression of the gene during the time course of the experiment for BT20 cells (BT20). Positive values indicate upregulation of the gene, and negative (−) values indicate downregulation. This comparison shows that genes differentially regulated in vitro by EGF treatment of BT20 cells are also differentially regulated in vivo in breast carcinoma. These genes may be useful in diagnosing and monitoring the progression of breast cancer and the response to treatment.

X Expression of the Encoded Protein

Expression and purification of a protein encoded by a cDNA of the invention is achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, such as BL21(DE3). Antibiotic resistant bacteria express the protein upon induction with IPTG. Expression in eukaryotic cells is achieved by infecting *Spodoptera frugiperda* (Sf9) insect cells with recombinant baculovirus, *Autographica californica* nuclear polyhedrosis virus. The polyhedrin gene of baculovirus is replaced with the cDNA by either homologous recombination or bacterial-mediated transposition involving transfer plasmid intermediates. Viral infectivity is maintained and the strong polyhedrin promoter drives high levels of transcription.

For ease of purification, the protein is synthesized as a fusion protein with glutathione-S-transferase (GST; APB) or a similar alternative such as FLAG. The fusion protein is purified on immobilized glutathione under conditions that maintain protein activity and antigenicity. After purification, the GST moiety is proteolytically cleaved from the protein with thrombin. A fusion protein with FLAG, an 8-amino acid peptide, is purified using commercially available monoclonal and polyclonal anti-FLAG antibodies (Eastman Kodak, Rochester N.Y.).

XI Production of Specific Antibodies

A denatured protein from a reverse phase HPLC separation is obtained in quantities up to 75 mg. This denatured protein is used to immunize mice or rabbits following standard protocols. About 100 μg is used to immunize a mouse, while up to 1 mg is used to immunize a rabbit. The denatured protein is radioiodinated and incubated with murine B-cell hybridomas to screen for monoclonal antibodies. About 20 mg of protein is sufficient for labeling and screening several thousand clones.

In another approach, the amino acid sequence translated from a cDNA of the invention is analyzed using PROTEAN software (DNASTAR) to determine regions of high antigenicity, essentially antigenically-effective epitopes of the protein. The optimal sequences for immunization are usually at the C-terminus, the N-terminus, and those intervening, hydrophilic regions of the protein that are likely to be exposed to the external environment when the protein is in its natural conformation. Typically, oligopeptides about 15 residues in length are synthesized using an ABI 431 peptide synthesizer (Applied Biosystems) using Fmoc-chemistry and then coupled to keyhole limpet hemocyanin (KLH; Sigma Aldrich) by reaction with M-maleimidobenzoyl-N-hydroxysuccinimide ester. If necessary, a cysteine may be introduced at the N-terminus of the peptide to permit coupling to KLH. Rabbits are immunized with the oligopeptide-KLH complex in complete Freund's adjuvant. The resulting antisera are tested for antipeptide activity by binding the peptide to plastic, blocking with 1% BSA, reacting with rabbit antisera, washing, and reacting with radioiodinated goat anti-rabbit IgG.

Hybridomas are prepared and screened using standard techniques. Hybridomas of interest are detected by screening with radioiodinated protein to identify those fusions producing a monoclonal antibody specific for the protein. In a typical protocol, wells of 96 well plates (FAST, Becton-Dickinson, Palo Alto Calif.) are coated with affinity-purified, specific rabbit-anti-mouse (or suitable anti-species Ig) antibodies at 10 mg/ml. The coated wells are blocked with 1% BSA and washed and exposed to supernatants from hybridomas. After incubation, the wells are exposed to radiolabeled protein at 1 mg/ml. Clones producing antibodies bind a quantity of labeled protein that is detectable above background.

Such clones are expanded and subjected to 2 cycles of cloning at 1 cell/3 wells. Cloned hybridomas are injected into pristane-treated mice to produce ascites, and monoclonal antibody is purified from the ascitic fluid by affinity chromatography on protein A (APB). Monoclonal antibodies with affinities of at least $10^8$ $M^{-1}$, preferably $10^9$ to $10^{10}$ $M^{-1}$ or stronger, are made by procedures well known in the art.

XII Purification of Naturally Occurring Protein Using Specific Antibodies

Naturally occurring or recombinant protein is substantially purified by immunoaffinity chromatography using antibodies specific for the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA or fragments thereof and the protein or portions thereof are labeled with $^{32}$P-dCTP, Cy3-dCTP, Cy5-dCTP (APB), or BIODIPY or FITC (Molecular Probes), respectively. Candidate molecules or compounds previously arranged on a substrate are incubated in the presence of labeled nucleic or amino acid. After incubation under conditions for either a cDNA or a protein, the substrate is washed, and any position on the substrate retaining label, which indicates specific binding or complex formation, is assayed. The binding molecule is identified by its arrayed position on the substrate. Data obtained using different concentrations of the nucleic acid or protein are used to calculate affinity between the labeled nucleic acid or protein and the bound molecule. High throughput screening using very small assay volumes and very small amounts of test compound is fully described in Burbaum et al. U.S Pat. No. 5,876,946.

TABLE 1

| SEQ ID NO: | Genbank ID | Genbank Description | BC1 | BC2 | BC3 | BC4 | BC5 | BC6 | BC7 | BT20 |
|---|---|---|---|---|---|---|---|---|---|---|
| 1 | 609301 | Human keratin 5 (KRT5) gene, intron 8, 5' end. | −2.4 | 2.0 | −7.1 | −2.8 | −2.1 | −3.8 | −4.2 | −3.6 |
| 2 | 531159 | Human dihydrodiol dehydrogenase mRNA, complete cds. | −4.3 | −4.8 | −1.7 | −4.1 | −3.4 | −3.4 | −7.8 | −9.9 |
| 3 | 4500003 | Human bile salt-activated lipase (BAL) mRNA, complete cds | −3.4 | −1.4 | −1.5 | −2.0 | −2.4 | −2.3 | −1.0 | −2.2 |
| 4 | 180947 | Human carboxylesterase mRNA, complete cds | −4.1 | −3.2 | −3.1 | −3.3 | −2.5 | −2.3 | 1.1 | −4.1 |
| 5 | 219899 | Human mRNA for long-chain acyl-CoA synthetase. | −1.7 | −3.3 | 1.2 | −2.4 | −1.3 | −2.0 | −2.3 | −2.2 |
| 6 | 688296 | brain-expressed HHCPA78 | −4.4 | −1.4 | −4.0 | −2.1 | −1.7 | −3.0 | −1.5 | −2.8 |
| 7 | 4105412 | GC4; RTP | −6.8 | −4.6 | −12 | −6.3 | −5.6 | −10 | −5.2 | −2.4 |
| 8 | 1916005 | Human eyes absent homolog (Eab1) mRNA, complete cds | −2.4 | −1.9 | −4.9 | −2.0 | −2.9 | −2.3 | −2.6 | −2.4 |
| 9 | 3676496 | Human mRNA for 6-phosphofructo-2-kinase/fructose-2,6-bisphosphatase | −1.7 | −2.2 | −1.7 | −3.2 | −2.9 | −3.1 | −3.7 | −2.1 |
| 10 | 1621606 | Human neogenin mRNA, complete cds. | −3.2 | −1.1 | −2.1 | −2.3 | −1.9 | −2.3 | −1.6 | −2.5 |
| 11 | 1469919 | Human tumor protein D53 (TPD52L1) mRNA, partial cds. | −2.8 | −2.2 | 1.2 | −2.2 | −2.0 | −3.2 | −1.6 | −2.4 |
| 12 | | Incyte Unique | −1.6 | −1.5 | −2.3 | −2.3 | −2.5 | −1.7 | −2.1 | −3.4 |
| 13 | | Incyte Unique | 3.6 | 1.8 | 1.1 | 2.1 | −1.1 | 6.9 | 5.5 | 2.2s |
| 14 | | Incyte Unique | −3.5 | −1.1 | −3.1 | −2.0 | −2.2 | −5.1 | −1.8 | −3.3 |
| 15 | | Incyte Unique | −2.4 | −1.2 | −3.4 | −1.8 | −1.5 | −2.0 | −2.7 | −2.4 |
| 16 | | Incyte Unique | −5.7 | −1.3 | −4.3 | −3.6 | −2.0 | −5.8 | −1.8 | −3.5 |

What is claimed is:

1. A combination comprising a plurality of cDNAs, wherein the plurality of cDNAs consists of SEQ ID NOs: 1–16 or their complements.

2. The combination of claim 1, wherein the cDNAs are immobilized on a substrate.

3. A high throughput method for detecting differential expression of one or more cDNAs in a sample containing nucleic acids, the method comprising:
   (a) hybridizing the substrate of claim 2 with nucleic acids of the sample, thereby forming one or more hybridization complexes;
   (b) detecting the hybridization complexes; and
   (c) comparing the hybridization complexes with those of a standard, wherein differences between the standard and sample hybridization complexes indicate differential expression of cDNAs in the sample.

4. The method of claim 3, where in the nucleic acids of the sample are amplified prior to hybridization.

5. A high throughput method of screening a plurality of molecules or compounds to identify a ligand which specifically binds a cDNA, the method comprising:
   (a) combining the combination of claim 1 with the plurality of molecules or compounds under conditions to allow specific binding; and
   (b) detecting specific binding between each cDNA and at least one molecule or compound, thereby identifying a ligand that specifically binds to each cDNA.

6. The method of claim 5 wherein the plurality of molecules or compounds are selected from DNA molecules, RNA molecules, peptide nucleic acid molecules, mimetics, peptides, transcription factors, repressors, and regulatory proteins.

* * * * *